United States Patent
Thomas et al.

(10) Patent No.: US 9,633,472 B2
(45) Date of Patent: Apr. 25, 2017

(54) MASTER MODEL FOR DATA RELATED TO A SPATIAL REGION

(71) Applicants: Mark Ivan Thomas, Auckland (NZ); Matthew James Easlea, Brisbane (AU)

(72) Inventors: Mark Ivan Thomas, Auckland (NZ); Matthew James Easlea, Brisbane (AU)

(73) Assignee: SAP SE, Walldorf (DE)

( * ) Notice: Subject to any disclaimer, the term of this patent is extended or adjusted under 35 U.S.C. 154(b) by 519 days.

(21) Appl. No.: 14/132,294

(22) Filed: Dec. 18, 2013

(65) Prior Publication Data
US 2015/0170411 A1 Jun. 18, 2015

(51) Int. Cl.
*G06T 17/00* (2006.01)
*G06F 19/26* (2011.01)
*G01V 99/00* (2009.01)

(52) U.S. Cl.
CPC ............. *G06T 17/00* (2013.01); *G06F 19/26* (2013.01); *G01V 99/00* (2013.01)

(58) Field of Classification Search
CPC ......... G06T 15/00; G06T 17/00; G06T 17/05; G06T 19/00; G06T 19/20; G06F 19/00; G06F 19/26; G01V 99/00
See application file for complete search history.

(56) References Cited

U.S. PATENT DOCUMENTS

| | | | | |
|---|---|---|---|---|
| 5,646,844 A | * | 7/1997 | Gudat | E01C 19/004 701/409 |
| 7,796,823 B1 | * | 9/2010 | Budagavi | G06T 9/00 382/232 |
| 2002/0124171 A1 | * | 9/2002 | Rhoads | G01C 11/00 713/176 |
| 2004/0158355 A1 | * | 8/2004 | Holmqvist | G05D 1/0236 700/245 |
| 2007/0195011 A1 | * | 8/2007 | Hatori | F41H 11/16 345/2.1 |
| 2011/0148856 A1 | * | 6/2011 | Sprock | E02F 9/2054 345/419 |
| 2013/0070962 A1 | * | 3/2013 | Yankun | G06T 7/20 382/103 |
| 2013/0179026 A1 | * | 7/2013 | McClure | A01B 69/008 701/25 |

* cited by examiner

*Primary Examiner* — Ke Xiao
*Assistant Examiner* — Jed-Justin Imperial
(74) *Attorney, Agent, or Firm* — Fish & Richardson P.C.

(57) ABSTRACT

The present disclosure involves systems, software, and computer-implemented methods for providing a master model for data about a spatial region. An example method includes identifying a master model associated with a spatial region, the master model including a plurality of pixels, each pixel corresponding to a particular portion of the spatial region and including a length and a width for the particular portion of the spatial region; identifying a data set including values of a physical property of at least a portion of the spatial region for a particular time; determining, based at least in part on the data set, a set of values of the physical property including a value for each pixel in the master model; and storing the set of values of the physical property as a value for each pixel.

14 Claims, 6 Drawing Sheets

MASTER MODEL FOR DATA RELATED TO A SPATIAL REGION

BACKGROUND

The present disclosure involves systems, software, and computer-implemented methods for providing a master model for data about a spatial region.

In applications working with spatial regions (such as mining, oil and gas exploration, medical procedures, etc.) different measurements associated with the same spatial region may be acquired from different data sources. These data sources may be sensors, design programs, diagnostic equipment, or other types of data sources. In some cases, the data sources may provide their data in different formats and at different resolutions.

SUMMARY

The present disclosure involves systems, software, and computer-implemented methods for providing a master model for data about a spatial region. In one general aspect, an example method includes identifying a master model associated with a spatial region, the master model including a plurality of pixels, each pixel corresponding to a particular portion of the spatial region and including a length and a width for the particular portion of the spatial region; identifying a data set including values of a physical property of at least a portion of the spatial region for a particular time; determining, based at least in part on the data set, a set of values of the physical property including a value for each pixel in the master model; and storing the set of values of the physical property as a value for each pixel.

While generally described as computer-implemented software embodied on non-transitory, tangible media that processes and transforms the respective data, some or all of the aspects may be computer-implemented methods or further included in respective systems or other devices for performing this described functionality. The details of these and other aspects and implementations of the present disclosure are set forth in the accompanying drawings and the description below. Other features, objects, and advantages of the disclosure will be apparent from the description and drawings, and from the claims.

DETAILED DESCRIPTION

The present disclosure involves systems, software, and computer-implemented methods for providing a master model for data about a spatial region.

In applications working with spatial regions, different types of data from different data sources may be analyzed to make decisions regarding the development or maintenance of the particular spatial region. In some cases, the different types of data may be different measurements taken of the spatial region, such as, for example, topological surveys, chemical composition studies, porosity studies, seismic exploration data, or other types of data. In some cases, each type of data may be stored in a different format and may require a separate application in order to be viewed by a user. Accordingly, cross-referencing the data sets against one another may be difficult without an integrated view including the different sets for comparison.

The present disclosure describes a solution in which a particular spatial region is associated with a master model dividing the spatial region into a number of pixels. Each of the different data sets for the particular spatial region is converted into a representation based on this master model. Subsequent data from the same source may be stored as a set of deltas from the original representation of the data based on the master model, so that only the portions of the data that change are stored. By storing the data sets according to the same master model, it may be possible to present data from different sources in a common view such that data can easily be compared and cross-referenced.

The present solution provides several potential advantages. By storing data from the different sources according to the same master model, the user may be presented with an integrated view of data from several sources. By storing the changes in the different data sets through time, a historical view of the characteristics of the spatial region may be present the user, such as in the form of an animated representation showing the change in the data through time. Further, by applying the compression techniques described herein, the data may be stored efficiently and at a low cost.

Figure 1:
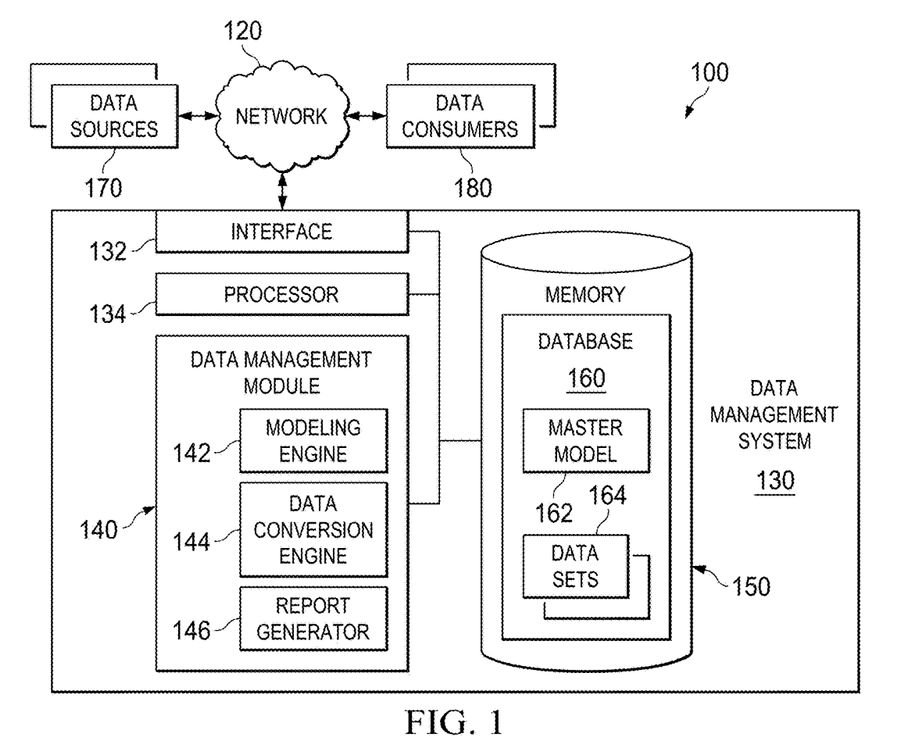
FIG. 1 is a block diagram illustrating an example environment for providing a master model for data about a spatial region.

FIG. 1 is a block diagram illustrating an example environment for providing a common model for data about a spatial region. As shown, the environment 100 includes a network 120. One or more data sources 170 and one or more data consumers 180 are connected to the network 120. A data management system 130 is also connected to the network 120.

In operation, data regarding his particular spatial region is received from the one or more data sources 170 via the network 120 at the data management system 130. The data may be measurements or other data collected from the spatial region, such as surveying data, height data, chemical composition data, or other types of data. The data received from the data sources 170 may also include design data associated with plans or designs for the spatial region, such as development plans, mining plans, construction plans, or other types of design data. The data management system 130 may receive these different types of data from the one or more data sources 170 and transform the different types of data into representations based on a master model associated with speech region. In some implementations, the master model may be created by separating the spatial region into a set of pixels, each pixel representing a certain area of the spatial region. For example, a mining site with dimensions of 100 meters (m)×100 m may be associated with a master model including 10,000 1 m×1 m pixels. In some implementations, the data management system 130 converts data at different resolutions to match the master model. For example, if data received from one of the data sources 170 includes readings taken at a higher resolution than the 10,000 1 m×1 m pixels in our example master model, the data management system 130 may convert the data into a series of measurements each corresponding to one of the 10,000 pixels. The data management system 130 may perform such conversion by performing a mathematical operation or operations on the data, such as taking an average of the data for each pixel, finding a maximum value of the data for each pixel, or any other appropriate operation operations. If the data received is of a lower resolution than the master model, the data management system 130 may convert the data into a series including a value for each pixel in the master model.

The data stored in terms of the master model may be stored as raster images, wherein each of the pixels in the master model is associated with a value representing the data in the data set. For example, height data for the example mining site discussed above may be stored as a 100×100 pixel raster image with different grayscale values for each pixel representing the height of the area of the mining site represented by the pixel.

When additional data is received from one of the data sources 170, the data management system 130 may represent this new data as a set of changes or deltas from an original data set stored in terms of the master model. For example, if a new data set indicates a change in the height of the mining site at only 10 pixels in the master model, this new height data set may be stored as a set of deltas of the original base data set. Additional data sets may also be stored as sets of deltas. Compression algorithms, such as lossy or lossless algorithms used in image or video compression, maybe used to compress the various data sets and sets of deltas stored in terms of a master model.

The data set stored by the data management system 130 in terms of the common master model may be provided to one or more data consumers 180. Since these data sets are normalized in terms of the common master model, the different types of data may be presented together in a common report to show an integrated view of the spatial region. For example, height data and porosity data of the mining site discussed above may both be stored in terms of the same 10,000 pixel master model. An interface, such as one of the data consumers 180, may present the height data and the porosity data of the mining site in a common interface since both data sets have been normalized to use the same master model.

As shown, environment 100 includes the data management system 130. As discussed above, the data management system 130 is operable to receive data about the spatial region from the one or more data sources 170, to convert the data into a representation in terms of a master model associated with the spatial region, and to provide the data to one or more data consumers 180. In some implementations, the data management system 130 is a server or set of servers connected to the network 120 and is operable to receive the data from the data source 170 over the network 120 and provide the data in terms of the master model to the data consumers 180 over the network 120. The data management system 130 may also be operable to receive data from the data sources 170 directly, such as over a data bus or from sensors taking measurements of the spatial region. The data management system 130 may also be operable to provide data according to the master model and reports including multiple types of data to users over the network 120, such as through a web browser.

As used in the present disclosure, the term "computer" is intended to encompass any suitable processing device. For example, although FIG. 1 illustrates a data management system 130, environment 100 can be implemented using two or more servers, as well as computers other than servers, including a server pool. Indeed, data management system 130 may be any computer or processing device such as, for example, a blade server, general-purpose personal computer (PC), Mac®, workstation, UNIX-based workstation, or any other suitable device. In other words, the present disclosure contemplates computers other than general purpose computers, as well as computers without conventional operating systems. Further, illustrated data management system 130 may be adapted to execute any operating system, including Linux, UNIX, Windows, Mac OS®, Java™, Android™, iOS or any other suitable operating system. According to one implementation, data management system 130 may also include or be communicably coupled with an e-mail server, a Web server, a caching server, a streaming data server, and/or other suitable server.

The data management system 130 also includes an interface 132, a processor 134, and a memory 150. The interface 132 is used by the data management system 130 for communicating with other systems in a distributed environment—including within the environment 100—connected to the network 120; for example, the clients 180, as well as other systems communicably coupled to the network 120 (not illustrated). Generally, the interface 132 comprises logic encoded in software and/or hardware in a suitable combination and operable to communicate with the network 120. More specifically, the interface 132 may comprise software supporting one or more communication protocols associated with communications such that the network 120 or interface's hardware is operable to communicate physical signals within and outside of the illustrated environment 100.

As illustrated in FIG. 1, the data management system 130 includes a processor 134. Although illustrated as a single processor 134 in FIG. 1, two or more processors may be used according to particular needs, desires, or particular implementations of environment 100. Each processor 134 may be a central processing unit (CPU), a blade, an application specific integrated circuit (ASIC), a field-programmable gate array (FPGA), or another suitable component. Generally, the processor 134 executes instructions and manipulates data to perform the operations of the data management system 130. Specifically, the processor 134 may execute the functionality required to receive and respond to requests from the clients 180.

The data management system 130 includes a data management module 140. In operation, the data management module 140 may create and maintain a master model of the spatial region. In some implementations, the data management module 140 may create and maintain multiple master models associated with multiple spatial regions. The data management module 140 may create a master model by examining data associated with the spatial region, such as surveying data, mapping data, or any other type of data that serves to define the physical structure or topology of the spatial region.

The data management module 140 may also receive data about the spatial region from the one or more data sources 170. In some implementations, the data management module 140 may be operable to convert the data received into representations based upon the master model. The data manager module 140 may also be operable to provide data based on the master model to the one or more data consumers 180.

Data management module 140 includes a modeling engine 142. In operation, the modeling engine 142 creates the master model associated with a given spatial region, and stores the master model for later use, such as in the database 160 as master model 162. In some implementations, the modeling engine 142 may create the master model automatically given mapping or topology data about a spatial region. The modeling engine 142 may also take as input parameters describing attributes of the master model to be generated, such as, for example the resolution of the master model (e.g., the number of pixels in which to divide the spatial region), the size of each pixel in the master model, dimensions of each pixel in the master model, or other parameters.

In some cases, the modeling engine 142 may create the master model based on data received from one of the data sources 170. For example, the modeling engine 142 may receive topological data mapping particular spatial region from one of the data sources 170. From this data, the modeling engine 142 may create a master model associated with the spatial region by examining the various data points in the data set. In such a case, the actual values for the different areas of the spatial region would then be stored in a representation of the master model, such as, for example, as a raster image with the color values of each pixel corresponding to the values in the data set.

The data manager module 140 also includes a data conversion engine 144. In operation, the data conversion engine 144 receives data from the one or more data sources 170 and converts the data from its native format into a representation based on the master model associated with the particular spatial region corresponding to the data. For example, the data conversion engine 144 may receive chemical composition data associated with spatial region at a first resolution. The data conversion engine 144 may convert the chemical composition data into a resolution matching the master model associated with spatial region for the data. Such conversion may involve determining a value for each pixel in the master model from the chemical composition data. The data conversion engine 144 may then receive porosity data from a second one of the data sources 170. The porosity data may be at a second resolution different than the first resolution and different than the resolution of the master model. The data conversion engine 144 may convert the porosity data into a representation based on the master model and at the resolution of the master model.

Each representation may include an indication of the time the data was acquired, such that the different data sets from a single source may be "played back" to observe a progression of the data through time. As each representation is associated with a time, a user may request a snapshot of the spatial region data for a particular time to view the state of the spatial region at that time. Such functionality may be useful when performing backwards-looking analysis on a spatial region, such as a safety audit after an accident.

In some cases, the master model may be a three-dimensional master model, such that voxels (three-dimensional pixels) are used to define the master model. In such cases, each voxel in the master model can include, for example, a length, a width, and a height component. Even when using a two-dimensional master model, three-dimensional representations of the data sets may be presented by cross-referencing a height data set stored according to the two-dimensional master model with another data set stored according to the two-dimensional master model (such as a porosity data set).

In some implementations, the data conversion engine 144 may create raster images based on the master model as the representations of the different data sets received from the data sources 170. The data conversion engine 144 may also store subsequent sets of data from the same source as sets of deltas from an original master model representation associated with the data source. In such a manner, storage space within the database 160 may be saved, as only changes to the original data set are stored. In some implementations, lossy or lossless compression algorithms used for video encoding or still image encoding may be used to provide compression between representations based on the master model for the same data source. For example, each raster image representation may be treated as a frame within a video stream, and may be compressed according to known techniques. Such compression schemes may include, but are not limited to, Motion Picture Expert Group (MPEG) compression, Joint Picture Expert Group (JPEG), or other compression schemes.

In addition to data sets involving measurements of properties of the spatial region, the data received from the one or more data sources 170 may also include position data associated with equipment within the spatial region. For example, within a mining site it may be advantageous to track the position of vehicles, excavation equipment, temporary buildings, or other equipment. Such position data may be processed by the data conversion engine 144, and stored as a representation based on the master model for the spatial region in the same manner as other types of data. For example, the data conversion engine 144 may store a raster image based on the master model for the mining site with black pixels indicating the position of equipment within the site.

The data management module 140, as illustrated, also includes a report generator 146. In operation, the report generator 146 may be operable to provide data based on the master model for spatial region to the one or more data consumers 180. In some cases, the report generator 146 may provide raster images based on the master model to the one or more data consumers 180, along with an indication of what the color data in the images means. The report generator 146 may also provide views of how the different data sets have changed through time as sets of raster images, or as compressed sets of raster images, such as image streams were video streams. In some implementations, the report generator 146 may receive requests from the one or more data consumers 180 for different data sets, and respond with the requested data sets. The report generator 146 may provide a web interface to respond to user requests for specific data sets.

In some cases, the report generator 146 may be operable to display multiple data sets a star on the master model measuring different attributes of the spatial region at a time. For example, the report generator 146 may display a three-dimensional representation of the spatial region with multiple sets of data overlaid on one another. In some implementations, the report generator 146 may use a height data set associated with the spatial region in order to apply three dimensional characteristics to data sets associated with the spatial region.

In some cases, the master model may be a three-dimensional master model, such that voxels (three-dimensional pixels) are used to define the master model, each voxel including a length, a width and a height component. In such a case, each voxel may include a specific height component, or maybe assumed cubic such that the length, width, and height are equal. Such a three-dimensional master model may be useful for modeling spatial regions with characteristics occurring at different heights, such as underground mines. For example, a three dimensional master model may be created for an underground mine, with voxels representing different portions of the mine. Data sets received from different data sources may be converted into sets of values including measurements for each of the voxels in the master model. The values may be stored as color values for each of the voxels, similar to the techniques described herein relative to the pixel-based master model.

Regardless of the particular implementation, "software" may include computer-readable instructions, firmware, wired and/or programmed hardware, or any combination thereof on a tangible medium (transitory or non-transitory, as appropriate) operable when executed to perform at least the processes and operations described herein. Indeed, each software component may be fully or partially written or described in any appropriate computer language including C, C++, Java™, Visual Basic, assembler, Perl®, any suitable version of 4GL, as well as others. While portions of the software illustrated in FIG. 1 are shown as individual modules that implement the various features and functionality through various objects, methods, or other processes, the software may instead include a number of sub-modules, third-party services, components, libraries, and such, as appropriate. Conversely, the features and functionality of various components can be combined into single components as appropriate.

The data management system 130 also includes a memory 150 or multiple memories 150. The memory 150 may include any type of memory or database module and may take the form of volatile and/or non-volatile memory including, without limitation, magnetic media, optical media, random access memory (RAM), read-only memory (ROM), removable media, or any other suitable local or remote memory component. The memory 150 may store various objects or data, including caches, classes, frameworks, applications, backup data, business objects, jobs, web pages, web page templates, database tables, repositories storing business and/or dynamic information, and any other appropriate information including any parameters, variables, algorithms, instructions, rules, constraints, or references thereto associated with the purposes of the data management system 130. Additionally, the memory 150 may include any other appropriate data, such as VPN applications, firmware logs and policies, firewall policies, a security or access log, print or other reporting files, as well as others.

As illustrated in FIG. 1, memory 150 includes or references data and information associated with and/or related to providing the network service load control. As illustrated, memory 150 includes a database 160. The database 160 may be one of or a combination of several commercially available database and non-database products. Acceptable products include, but are not limited to, SAP® HANA DB, SAP® MaxDB, Sybase® ASE, Oracle® databases, IBM® Informix® databases, DB2, MySQL, Microsoft SQL Server®, Ingres®, PostgreSQL, Teradata, Amazon SimpleDB, and Microsoft® Excel, as well as other suitable database and non-database products. Further, database 160 may be operable to process queries specified in any structured or other query language such as, for example, Structured Query Language (SQL).

The database 160 includes a master model 162. In some implementations, the master model 162 for particular spatial region may be stored as a raster image with no color data. Such an image may define a grid of pixels onto which data from the one or more data sources 170 may be mapped.

Although a single master model 162 is shown in FIG. 1, the database 160 may include multiple master models corresponding to different spatial regions.

Database 160 also includes one or more data sets 164. Data sets 164 are representations of data sets received from the one or more data sources 170 is then converted to be based on the master model 162, as described relative to the data conversion engine 144 above. In some implementations, the data sets 164 are stored as raster images based on the master model 162 and sets of deltas from a base raster image representing subsequent data from the same data source. In some cases, the data sets 164 may include an indication of a type of data the particular raster image represents. The data sets 164 may also include metadata associated with the original data set.

As shown, the environment 100 includes one or more data sources 170. The data sources 170 may provide data associated with the spatial region for processing by the data management system 130. The data sources 170 may include, but are not limited to, CAT Mine Star, Runge Mine Scheduling, Maptech Vulcan Mine design software, Dassault GeoVia, GemCom, or other systems providing data about a particular spatial region.

Figure 2:
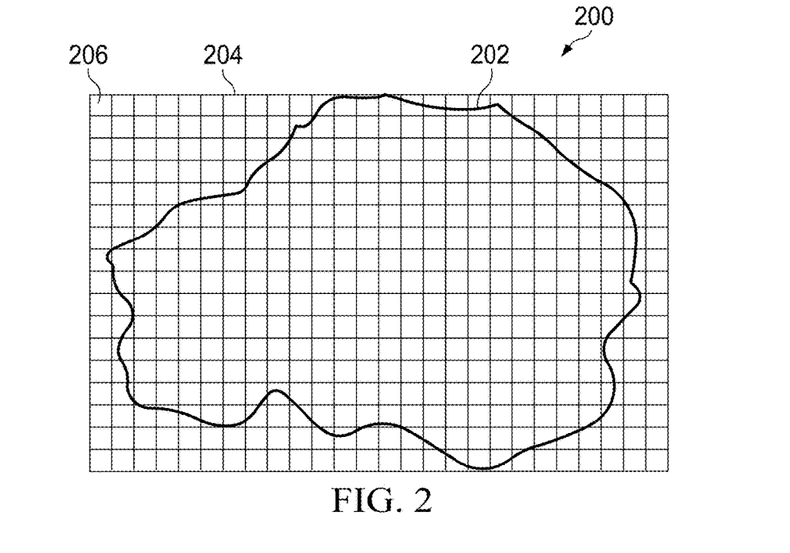
FIG. 2 shows an example master model for a spatial region.

FIG. 2 shows an example master model 204 for a spatial region 202. The master model 204 is made up of a number of pixels 206, each pixel representing a portion of the spatial region 202. For example, the spatial region 202 may be a mining site, and each pixel in the master model may represent a 1 m×1 m square of the mining site area. As the topology of the mining site changes over time (e.g., as the mine is excavated) survey data from the mining site may be stored as representations of the master model 204, such that a detailed picture of the progress of the mine excavation can be seen by examining the data.

Figure 3A:
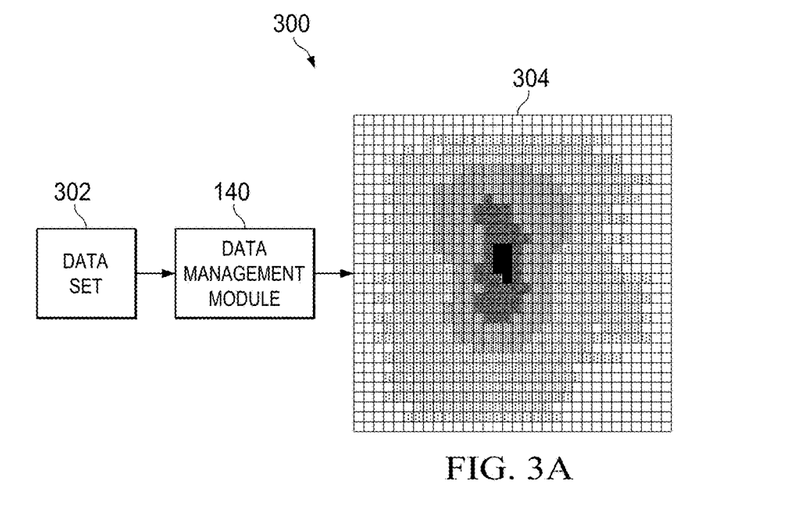
FIG. 3A shows a transformation of a data set into a representation based on a master model.

FIG. 3A shows a transformation of a data set into a representation based on a common model. As shown, the data set 302 is processed by the data management module 140 to produce a raster image 304 based on a master model of the spatial region. In the raster image 304, the colors of the different pixels represent the values from the data set 302 associated with the areas of the spatial region associated with each pixel. For example, the darker shades of gray in the raster image 304 may represent higher values from the data set 302, the lighter shades of gray may represent lower values.

Figure 3B:
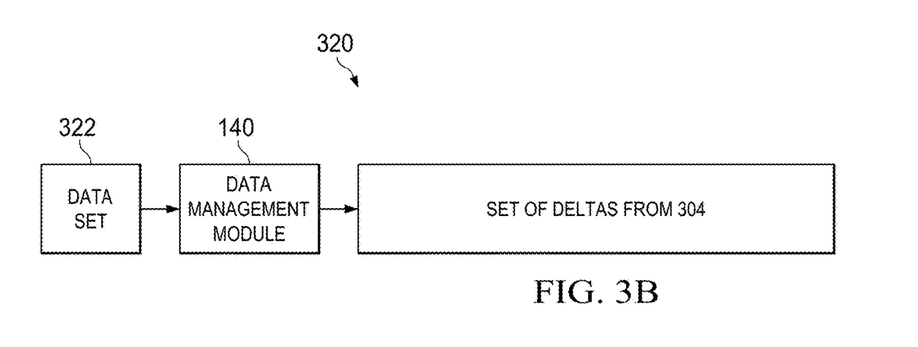
FIG. 3B shows a transformation of a data set into a set of deltas from an original data set.

FIG. 3B shows a transformation of a data set into a set of deltas from an original data set. Again, a data set 322 is read by the data management module 140. In the illustrated case, the data set 322 is a data set from the same source as the data set 302, such as a data set representing measurements taken at a later time. The data manager module 140 produces a set of deltas 324 representing the change in the data from the data set 302 to the data set 322. In some implementations, subsequent data sets may be stored is complete raster images based on the master model, and compressed at a later time by identifying differences between the raster images.

Figure 3C:
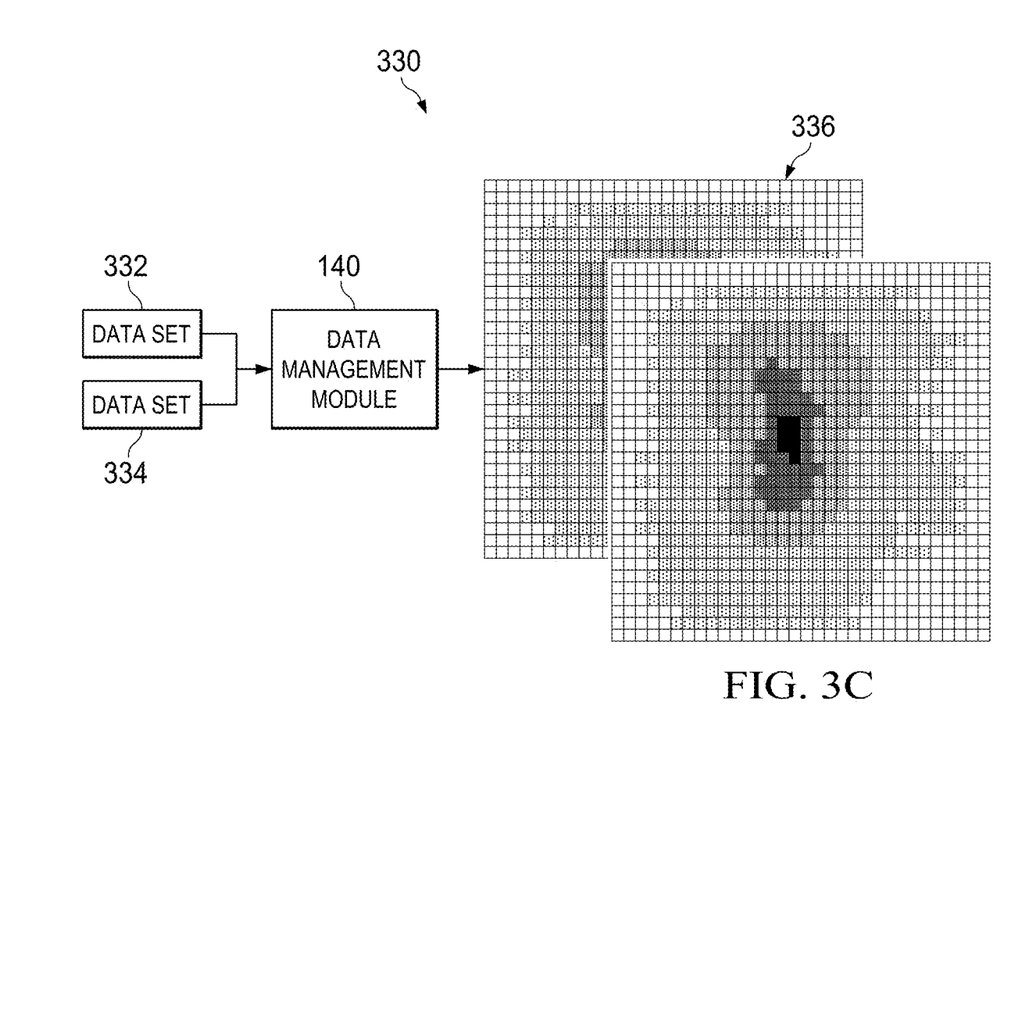
FIG. 3C shows two data sets from different sources transformed into two separate representations based on the same master model.

FIG. 3C shows two data sets from different sources transformed into two separate representations based on the same master model. Data sets 332 and 334 are received from different data sources at the data manager module 140. The data manager module 140 may produce separate raster images for the different data sets each of the raster images based on the same master model for the spatial region.

Figure 4:
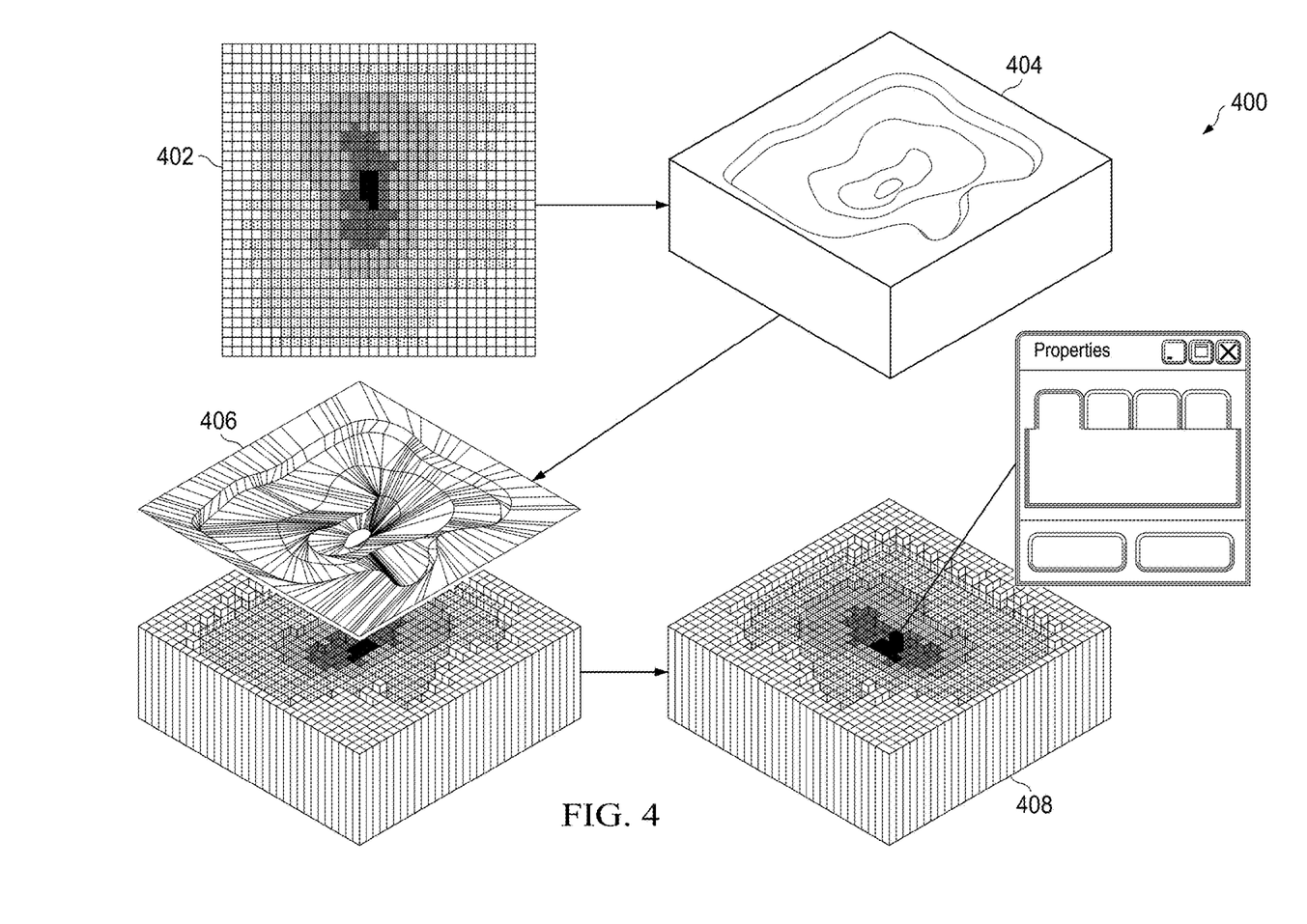
FIG. 4 shows data stored based on a common model being presented as a three dimensional representation.

FIG. 4 shows data stored based on a common model being presented as a three dimensional representation. Raster image 402 shows a two-dimensional representation of data associated with the spatial region based on a master model.

Three-dimensional model 404 may be generated from the raster image 402, such as in the case where the color data in the raster image indicates height of the different pixels. The three-dimensional model 404 may also be cross-referenced with the raster image 404 to produce a three-dimensional representation 406. The interactive representation 408 may allow the user to inspect different portions of the data set and see properties of different portions of the spatial region. As shown in the dialog box 410, varies attributes of the selected portion of the representation 408 are shown. Each of these attributes may be retrieved from the reputations of the various data sets based on the master model associated with spatial region.

Figure 5:
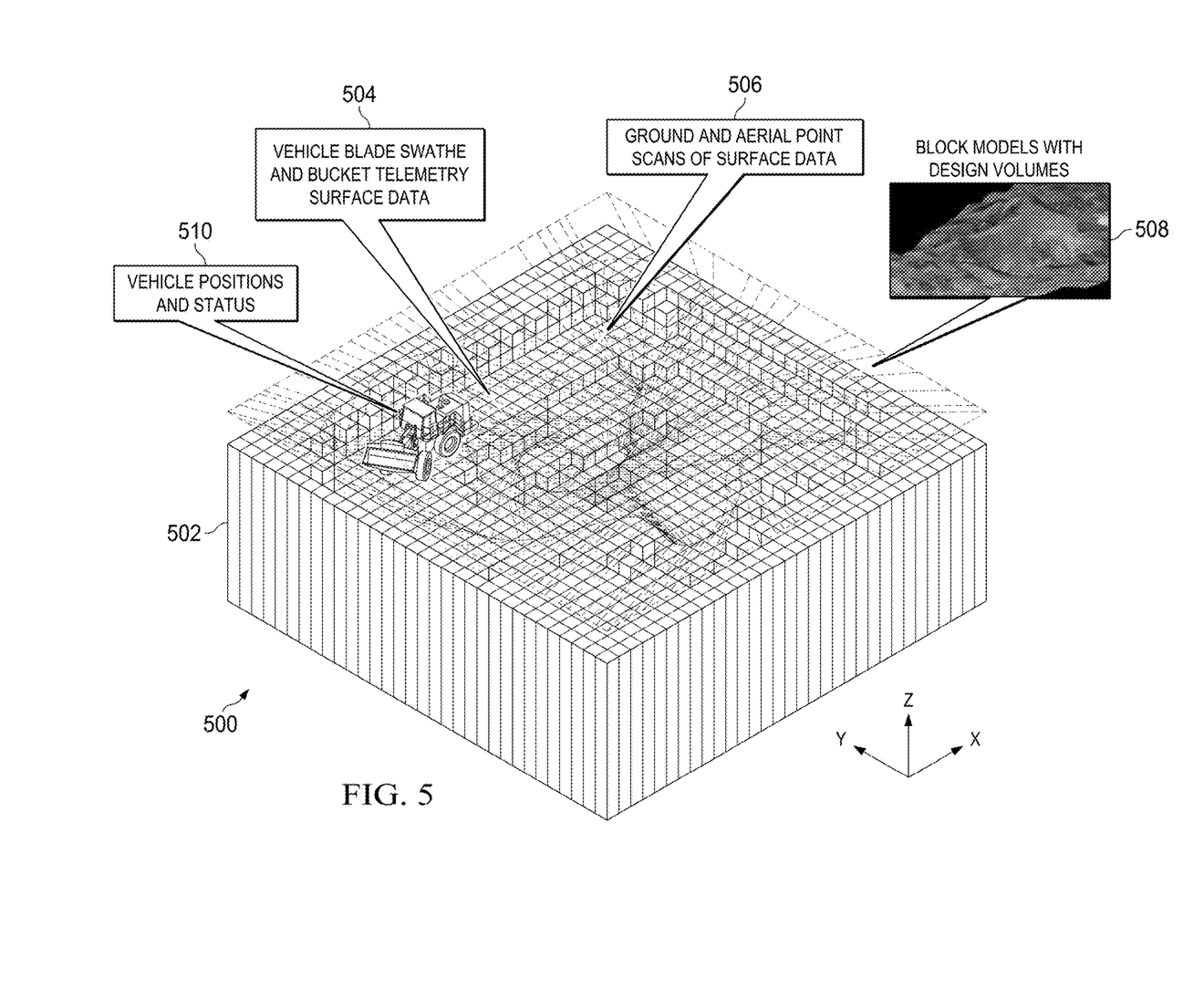
FIG. 5 shows data from different sources stored based on a common model being presented as a three dimensional representation.

FIG. 5 shows data from different sources stored based on a common model being presented as a three dimensional representation. The three-dimensional model 502 of the spatial region may be a three-dimensional master model including foxholes, or a height data set associated with a master model and cross-referenced with the other data set shown in FIG. 5. Data sets 504, 506, 508, and 510 are shown overlaid according to the common master model, such that all the data sets can be viewed in a three-dimensional representation at the same time. In the illustrated example, data set 504 includes vehicle blade swathe and bucket telemetry surface data. Data set 506 includes ground and aerial point scans of surface data. Data set 508 includes block models with design volumes. Data set 510 includes vehicle position and status data. In some implementations, other types of data sets may be displayed.

Figure 6:
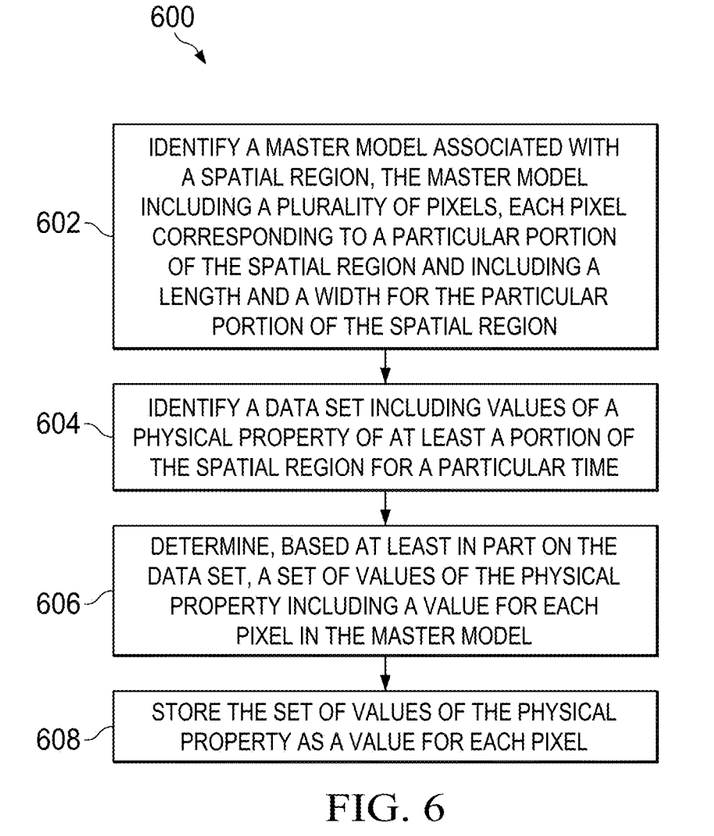
FIG. 6 is flow chart showing an example method for providing a common model for data about a spatial region.

FIG. 6 is flow chart showing an example method for providing a common model for data about a spatial region. For clarity of presentation, the description that follows generally describes method 600 in the context of FIG. 1. However, method 600 may be performed, for example, by any other suitable system, environment, software, and hardware, or a combination of systems, environments, software, and hardware, as appropriate. For example, one or more of the data management system, the client, or other computing device (not illustrated) can be used to execute method 600 and obtain any data from the memory of the client, data management system, or the other computing device (not illustrated).

At 602, a master model associated with a spatial region is identified. The master model may include a plurality of pixels, each pixel corresponding to a particular portion of the spatial region and including a link in a width for the particular portion of the spatial region. In some implementations, identifying the master model may include identifying a desired grid density associated with the master model, and determining a number of pixels to include in the master model based on the desired grid density.

At 604, a data set including values of up his physical property of at least a portion of the spatial region for particular time is identified. In some cases, the data set may associated with a data source including at least one of a design system, a point cloud scanning system, a voxel data source, a bore hole data source, an image capture data source, or a global positioning system. The physical property may include, but is not limited to, height, porosity, chemical concentration, designed height, or equipment position.

At 606, a set of values of the physical property is determined based at least in part on the data set, the set of values including a value for each pixel in the master model. For example, if the data set includes porosity measurements for the spatial region, the set of values may be determined by analyzing the data set to find a porosity value for each of the locations in the spatial region corresponding to each of the pixels in the master model.

At 608, the set of values of the physical property is stored as a value for each pixel. In some cases, the set of values are stored as a raster image representing the set of values, wherein a color value of each pixel represents a value of the physical property. In some implementations, the stored set of values may be provided to a data consumer. For example, the set of values of physical property may be provided to an external user interface for presentation in a three dimensional model representing the spatial region.

FIG. 7 is flow chart showing an example method for providing a common model for data about a spatial region. For clarity of presentation, the description that follows generally describes method 700 in the context of FIG. 1. However, method 700 may be performed, for example, by any other suitable system, environment, software, and hardware, or a combination of systems, environments, software, and hardware, as appropriate. For example, one or more of the data management system, the client, or other computing device (not illustrated) can be used to execute method 700 and obtain any data from the memory of the client, data management system, or the other computing device (not illustrated).

At 702, the set of values is stored as a first raster image. In some cases, the color value of each pixel in the raster image represents a value associated with that pixel. For example, a higher color value may indicate a higher value in the data set associated with that pixel.

At 704, a second data set is identified including values of the physical property of the spatial region for a second time. In some implementations, the second data set may be identified from the same data source as the data set described relative to FIG. 6. The second data set may represent a second reading of the physical property at a time later than the time of the original data set.

At 706, the second data set is analyzed to determine a second set of values of the physical property including a value for each pixel in the master model. The second raster image may be identified according to the techniques previously discussed.

At 708, a difference between the first raster image and the second raster image is determined. In some implementations, the difference is determined by comparing the first and second raster images pixel by pixel and determining which values are different. In some implementations, the difference may be represented as an image mask indicating the pixels that a change between the first raster image and the second raster image. For example, the image mask may include a color value of white for all pixels that have not changed, and a color value of black for all pixels that have changed.

At 710, the second set of values is stored as the difference between the first raster image and the second raster image. In some implementations, the difference is stored as a set of deltas associated with the pixels that have changed between the first raster image and the second raster image. By storing changes between the two images, the amount of stored data may be reduced.

In some implementations, the master model includes height data and is represented by a raster image including the color value for each of the pixels representing the height of the portion of the spatial region represented by the pixel. In some cases, the master may include a plurality of voxels instead of the plurality of pixels, each voxel further including a height for the particular portion of the spatial region.

The preceding figures and accompanying description illustrate example processes and computer implementable techniques. Environment 100 (or its software or other components) contemplates using, implementing, or executing any suitable technique for performing these and other tasks. These processes are for illustration purposes only and that the described or similar techniques may be performed at any appropriate time, including concurrently, individually, or in combination. In addition, many of the steps in these processes may take place simultaneously, concurrently, and/or in different order than as shown. Moreover, environment 100 may use processes with additional steps, fewer steps, and/or different steps, so long as the methods remain appropriate.

In other words, although this disclosure has been described in terms of certain implementations and generally associated methods, alterations and permutations of these implementations and methods will be apparent to those skilled in the art. Accordingly, the above description of example implementations does not define or constrain this disclosure. Other changes, substitutions, and alterations are also possible without departing from the spirit and scope of this disclosure.

What is claimed is:

1. A computer-implemented method executed by one or more processors, the method comprising:
    identifying a master model associated with a spatial region, the master model including a plurality of pixels, each pixel corresponding to a particular portion of the spatial region and including a length and a width for the particular portion of the spatial region, the master model associated with a first resolution;
    identifying a first data set including values of a physical property of at least a portion of the spatial region for a first time, the identified first data set identified in a native format and associated with a second resolution different than the first resolution;
    determining, based at least in part on the first data set, a first set of values of the physical property including a value for each pixel in the master model, wherein determining the first set of values of the physical property includes:
        converting the identified first data set from the native format associated with a second resolution to the first resolution associated with the master model;
        associating the first set of values of the physical property from the converted first data set as a value in the first resolution to the corresponding pixel in the master model;
    storing the first set of values of the physical property as a value for each pixel in the master model, wherein storing the set of values of the physical property includes storing the first set of values as a first raster image;
    identifying a second data set including values of the physical property of the spatial region for a second time, the identified second data set identified in the native format and associated with the second resolution;
    determining, based at least in part on the second data set, a second set of values of the physical property including a value for each pixel in the master model;
    identifying a second raster image representing the second set of values;
    determining a difference between the first raster image and the second raster image to identify a set of deltas between the first raster image and the second raster image;
    storing the set of deltas; and
    presenting the first set of values and the second set of values according to the master model, wherein presenting the first and second set of values comprises presenting an animated representation illustrating a change in the values from the first time to the second time by initially presenting the first raster image accordingly to the master model and subsequently presenting the first raster image modified by the set of deltas.

2. The method of claim 1, wherein identifying the master model includes:
    identifying a desired grid density associated with the master model; and
    determining a number of pixels to include in the master model based on the desired grid density.

3. The method of claim 1, wherein a color value for each pixel in the first raster image represents a value of the physical property.

4. The method of claim 1, wherein determining and storing the difference between the first raster image and the second raster image is performed using a lossy algorithm.

5. The method of claim 1, wherein the first set of values is associated with a first data source and the second set of values is associated with a second data source different than the first data source.

6. The method of claim 5, wherein the first and second data sources include at least one of a design system, a point cloud scanning system, a voxel data source, a bore hole data source, an image capture data source, or a global positioning system.

7. The method of claim 1, wherein the physical property is one of height, porosity, chemical concentration, designed height, or equipment position.

8. The method of claim 1, wherein the spatial region is a mine.

9. The method of claim 1, wherein the master model includes height data and is represented by a raster image including the color value for each of the pixels representing the height of the portion of the spatial region represented by the pixel.

10. The method of claim 1, wherein the plurality of pixels in the master model are a plurality of voxels, each voxel further including a height for the particular portion of the spatial region.

11. A non-transitory, computer-readable medium storing instructions operable when executed to cause at least one processor to perform operations comprising:
    identifying a master model associated with a spatial region, the master model including a plurality of pixels, each pixel corresponding to a particular portion of the spatial region and including a length and a width for the particular portion of the spatial region, the master model associated with a first resolution;
    identifying a first data set including values of a physical property of at least a portion of the spatial region for a first time, the identified first data set identified in a native format and associated with a second resolution different than the first resolution;
    determining, based at least in part on the first data set, a first set of values of the physical property including a value for each pixel in the master model, wherein determining the first set of values of the physical property includes:
        converting the identified first data set from the native format associated with a second resolution to the first resolution associated with the master model;

associating the first set of values of the physical property from the converted first data set as a value in the first resolution to the corresponding pixel in the master model; and storing the first set of values of the physical property as a value for each pixel in the master model, wherein storing the set of values of the physical property includes storing the first set of values as a first raster image;

identifying a second data set including values of the physical property of the spatial region for a second time, the identified second data set identified in the native format and associated with the second resolution;

determining, based at least in part on the second data set, a second set of values of the physical property including a value for each pixel in the master model;

identifying a second raster image representing the second set of values;

determining a difference between the first raster image and the second raster image to identify a set of deltas between the first raster image and the second raster image;

storing the set of deltas; and presenting the first set of values and the second set of values according to the master model, wherein presenting the first and second set of values comprises presenting an animated representation illustrating a change in the values from the first time to the second time by initially presenting the first raster image accordingly to the master model and subsequently presenting the first raster image modified by the set of deltas.

12. The computer-readable medium of claim 11, wherein identifying the master model includes:

identifying a desired grid density associated with the master model; and determining a number of pixels to include in the master model based on the desired grid density.

13. The computer-readable medium of claim 11, wherein a color value for each pixel in the first raster image represents a value of the physical property.

14. A system comprising:

memory for storing data; and one or more processors operable to perform operations comprising:

identifying a master model associated with a spatial region, the master model including a plurality of pixels, each pixel corresponding to a particular portion of the spatial region and including a length and a width for the particular portion of the spatial region, the master model associated with a first resolution;

identifying a first data set including values of a physical property of at least a portion of the spatial region for a first time, the identified first data set identified in a native format and associated with a second resolution different than the first resolution;

determining, based at least in part on the first data set, a first set of values of the physical property including a value for each pixel in the master model, wherein determining the first set of values of the physical property includes:

converting the identified first data set from the native format associated with a second resolution to the first resolution associated with the master model;

associating the first set of values of the physical property from the converted first data set as a value in the first resolution to the corresponding pixel in the master model; and storing the first set of values of the physical property as a value for each pixel in the master model, wherein storing the set of values of the physical property includes storing the first set of values as a first raster image;

identifying a second data set including values of the physical property of the spatial region for a second time, the identified second data set identified in the native format and associated with the second resolution;

determining, based at least in part on the second data set, a second set of values of the physical property including a value for each pixel in the master model;

identifying a second raster image representing the second set of values;

determining a difference between the first raster image and the second raster image to identify a set of deltas between the first raster image and the second raster image;

storing the set of deltas; and presenting the first set of values and the second set of values according to the master model, wherein presenting the first and second set of values comprises presenting an animated representation illustrating a change in the values from the first time to the second time by initially presenting the first raster image accordingly to the master model and subsequently presenting the first raster image modified by the set of deltas.

* * * * *